United States Patent [19]
Chu et al.

[11] Patent Number: 4,968,650
[45] Date of Patent: Nov. 6, 1990

[54] ZSM-5 CATALYSTS HAVING PREDOMINANTLY FRAMEWORK GALLIUM, METHODS OF THEIR PREPARATION, AND USE THEREOF

[75] Inventors: Cynthia T. Chu, Princeton Junction; Scott Han, Lawrenceville, both of N.J.

[73] Assignee: Mobil Oil Corporation, New York, N.Y.

[21] Appl. No.: 340,337

[22] Filed: Apr. 19, 1989

Related U.S. Application Data

[63] Continuation of Ser. No. 141,444, Jan. 7, 1988, abandoned, and a continuation of Ser. No. 258,091, Oct. 14, 1988, abandoned, which is a continuation of Ser. No. 777,049, Sep. 17, 1985, abandoned.

[51] Int. Cl.$^5$ .............................................. B01J 29/04
[52] U.S. Cl. ........................................ 502/61; 502/71; 502/77; 423/624; 423/330
[58] Field of Search ............................ 502/61, 71, 77; 423/624, 330

[56] References Cited

U.S. PATENT DOCUMENTS

| | | | |
|---|---|---|---|
| 3,702,886 | 11/1972 | Arganer et al. | 423/328 |
| 3,926,781 | 12/1975 | Gale | 208/115 |
| 3,970,544 | 7/1976 | Rosinski et al. | 208/111 |
| 4,056,575 | 11/1977 | Gregory et al. | 208/135 |
| 4,120,910 | 10/1978 | Chu | 260/673 |
| 4,134,823 | 1/1979 | Bertolacini | 208/65 |
| 4,157,356 | 6/1979 | Bulford et al. | 585/415 |
| 4,180,689 | 12/1979 | Davies et al. | 585/407 |
| 4,276,437 | 6/1981 | Chu | 585/467 |
| 4,347,394 | 8/1982 | Detz et al. | 585/419 |
| 4,350,835 | 9/1982 | Chester et al. | 585/415 |
| 4,392,989 | 7/1983 | Chu et al. | 585/415 |
| 4,482,774 | 11/1984 | Koetsier | 585/481 |
| 4,487,843 | 12/1984 | Telford et al. | 502/61 |
| 4,507,404 | 3/1985 | Minderhoud et al. | 208/65 |
| 4,524,140 | 6/1985 | Chang et al. | 502/61 |
| 4,808,295 | 2/1989 | Nemet-Mavrodin | 208/65 |
| 4,822,939 | 4/1989 | Chu | 585/408 |

FOREIGN PATENT DOCUMENTS

| | | |
|---|---|---|
| 50021 | 4/1982 | European Pat. Off. |
| 107876 | 5/1984 | European Pat. Off. |
| 133591 | 2/1985 | European Pat. Off. |
| 150105 | 7/1985 | European Pat. Off. |
| 223345 | 5/1987 | European Pat. Off. |
| 0116617 | 9/1980 | Japan .............................. 423/328 M |
| 2023562 | 1/1980 | United Kingdom ........... 423/328 M |
| 1561590 | 2/1980 | United Kingdom ........... 423/328 M |
| 840389 | 10/1984 | World Int. Prop. O. |

OTHER PUBLICATIONS

Journal of Catalysis, vol. 106, pp. 287–291, Academic Press, 1987, "Galosilicate Molecular Sieves: The Role of Framework and Nonframework Gallium on Catalytic Cracking Activity."

Primary Examiner—Chung Pak
Attorney, Agent, or Firm—Alexander J. McKillop; Charles J. Speciale; Marina V. Schneller

[57] ABSTRACT

Zeolite catalysts containing gallium, the gallium is primarily present in the framework of the catalyst and the catalyst contains little or no non-framework gallium; and methods for producing such catalysts by varying the reaction molar ratios of $SiO_2/Ga_2O_3$; and the use of such catalysts to produce high octane aromatics.

4 Claims, 2 Drawing Sheets

ZSM-5 CATALYSTS HAVING PREDOMINANTLY FRAMEWORK GALLIUM, METHODS OF THEIR PREPARATION, AND USE THEREOF

CROSS REFERENCE TO RELATED APPLICATIONS

This application is a continuation of Ser. No. 141,444, filed Jan. 7, 1988, now abandoned, and of Ser. No. 258,091, filed Oct. 14, 1988, now abandoned, which in turn is a continuation of Ser. No. 777,049, filed Sept. 17, 1985, now abandoned.

FIELD OF THE INVENTION

This invention relates to ZSM-5 catalysts containing gallium; the gallium is primarily present in the framework of the catalyst and the catalyst has little or no non-framework gallium. The invention also relates to methods of preparing such catalyst, and the use of the catalyst in the production of high-octane aromatic products.

BACKGROUND OF THE INVENTION

Zeolite catalysts have become widely-used in the processing of petroleum and in the production of various petrochemicals. Reactions such as cracking, hydrocracking, catalytic dewaxing, alkylation, dealkylation, transalkylation, isomerization, polymerization, addition, disproportionation and other acid-catalyzed reactions may be performed with the aid of these catalysts. Both natural and synthetic zeolites are known to be active for the reactions described above.

Early synthetic zeolites such as Zeolite A, X and Y and several mineral zeolites, chabazite, erionite, and mordenite, contain high silica/alumina ratios. Early laboratory research established that hydrolytic attack on framework aluminum atoms would cause loss of structural integrity (loss of crystallinity) of these zeolites. Additionally, the amount of alumina present appears directly related to acidity characteristics of zeolites. A correlation exists between the high acidity of such catalyst and the formation of coke in catalytic hydrocarbon processing using such catalysts. Coke formation increases the aging and reduces the stability of the catalysts. In order to overcome the deficiencies of the early zeolites, research was conducted to synthesize new zeolite structures having low aluminum atom content. Among the first successes was the production of Zeolites ZK-4 and ZK-5. Another success was the discovery of Zeolite ZSM-5, disclosed and claimed in U.S. Pat. No. 3,702,886. ZSM-5 catalysts are characterized by frameworks primarily composed of $SiO_2$, with occasional aluminum substitutions. These catalysts are more particularly identified by an X-ray diffraction pattern disclosed in U.S. Pat. Nos. 3,702,886, the disclosure of which is incorporated by reference herein.

Generally, ZSM-5 catalysts are prepared from reaction mixtures comprising sources of silica, alumina, alkali metals, water, and a template composed of an organic nitrogen-containing cation such as tetrapropylammonium hydroxide (TPAOH). A gel or sol prepared by mixing the above ingredients is digested in a temperature range of 150° C. to 200° C. for about 25 to 190 hours to form a crystalline zeolite containing framework silica and alumina having a silica:alumina ratio of at least 12. The ratio can exceed 10,000. The product is then heated to remove water and activated by replacing its sodium cations with non-metallic cations, such as hydrogen and ammonium, by cation-exchange.

Because of their shape selectivity and exceptionally high degree of thermal stability, ZSM-5 catalysts find use in a host of hydrocarbon conversion reactions. But, because of their low aluminum content, their catalytic activity is not as great as other zeolites having a higher aluminum content. To improve the catalytic activity of ZSM-5 catalysts, the catalyst can be prepared so that it contains a framework metal other than aluminum. It also is advantageous, at times, to synthesize a catalyst so that its activity is directed to a specific hydrocarbon reaction. The addition of non-framework metals sometimes has this effect. U.S. Pat. No. 3,702,886 discloses a method for producing a catalyst containing framework gallium, a [Ga]ZSM-5 catalyst. However, the product produced by the method of the '886 patent contains a quantity of non-framework gallium which is not suitable for purposes of this invention.

The present inventors have developed two methods for preparing a [Ga]ZSM-5 catalyst. The catalysts produced by the methods of the claimed invention contain gallium, and the gallium is primarily present in the framework of the catalyst, and the catalyst contains little or no non-framework gallium.

SUMMARY OF THE INVENTION

This invention relates to ZSM-5 catalysts having gallium primarily present in the framework of the catalyst and the catalyst contains little or no non-framework gallium. The invention also relates to their methods of preparation, and their use in the production of high-octane aromatic products. In accordance with the claimed invention, two separate methods are set forth for producing such catalysts. In a first method, gallium is added to the zeolite starting mixture in the form of salts so that an $SiO_2/Ga_2O_3$ molar ratio of greater than or equal to 100/1 is present in the reaction mixture. In a second method, gallium is added to the zeolite starting mixture in the form of salts so that an $SiO_2/Ga_2O_3$ molar ratio of less than 100/1 is present in the reaction mixture. Sodium sulfate is added to the reaction mixture when the $SiO_2/Ga_2O_3$ molar ratio is less than 100/1.

DESCRIPTION OF THE PREFERRED EMBODIMENTS

Figure 1:
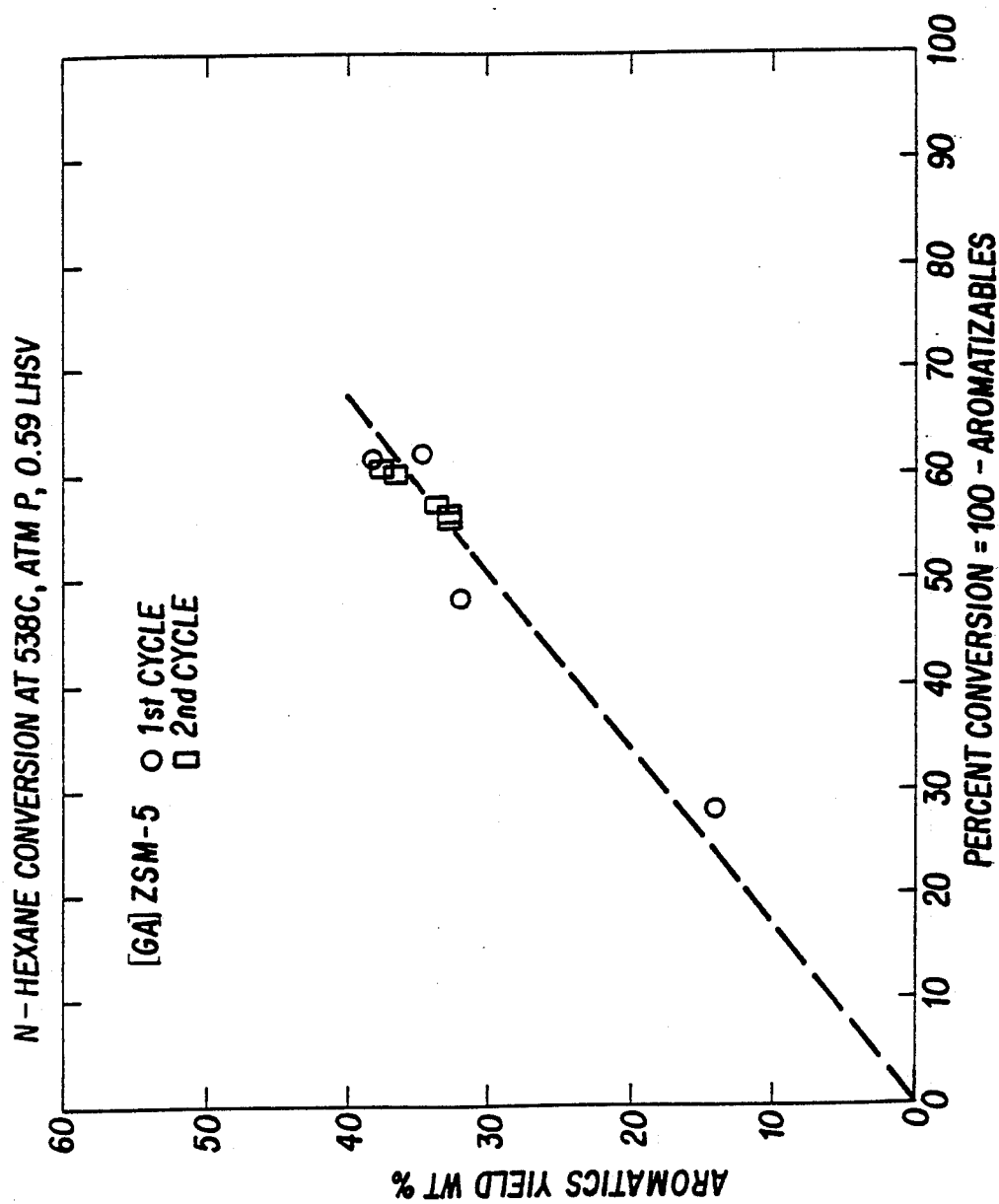
FIG. 1 is a plot showing percent conversion as weight percent yield of aromatics versus the percent conversion $100-C_2=+$ in the presence of the [Ga]ZSM-5 catalyst of the invention.

The novel process of this invention relates to the production of zeolites containing framework gallium; the gallium is primarily present in the framework of the catalyst, and the catalyst contains little or no non-framework gallium. The process involves directly synthesizing a ZSM-5 catalyst in the presence of gallium salts.

In a first embodiment, a [Ga]ZSM-5 catalyst is prepared so that a zeolite reaction mixture, from which the catalyst is obtained, contains $SiO_2/Ga_2O_3$ ratios of $\geq 100/1$ to $10,000/1$. The starting ratios used are also ratios of material obtained in the final product. Although $SiO_2/Ga_2O_3$ ratios of greater than $10,000/1$ can be used as starting ratios, catalyst containing $SiO_2/Ga_2O_3$ ratios of greater than $10,000/1$ really have no practical utility. So the upper limit is defined by the practical utility of such a catalyst. The zeolite reaction mixture may be essentially free of alumina and aluminum. Essentially free of alumina and aluminum, for the purposes of this invention, means that the crystalline product produced will only show the existence of aluminum as an impurity. That is, the silica sol used in the reaction mixture and even the gallium used in the reaction mixture will contain aluminum as an impurity. This impurity will show up in the final product.

The zeolite reaction mixture is prepared by mixing, for example, tetrapropylammonium bromide (TPABr) or any other organic template, with sodium hydroxide, a gallium compound, a silica-containing compound or a silica-containing mixture, in water. The zeolite reaction mixture has a composition of hydrogel molar ratios reported in Table I:

TABLE 1

| $SiO_2/Ga_2O_3$ | = | X |
| $H_2O/SiO_2$ | = | 40 |
| $OH^-/SiO_2$ | = | 0.05 |
| $Na^+/SiO_2$ | = | 0.05 |
| $TPA^+/SiO_2$ | = | 0.10 | wherein X varies from $\geq 100$ to $10,000$.

The reaction mixture is heated to a temperature of from 100 to 175° C. for a period of about six hours to sixty days. A preferred temperature range is from about 150° to 175° C. for twelve hours to eight days. The reaction is conducted in an autoclave and is digested with agitation until crystals form. The solid product is separated from the reaction medium by cooling the mixture to room temperature and then washing.

The crystal product is dried at elevated temperatures, for example, at 230° F. for eight to twenty-four hours or it is dried at room temperature under vacuum. The organic template is then burned off in a mixture of nitrogen and oxygen, or pure oxygen, at 1,000° F. for four hours. The catalyst is ion exchanged, for example, with $NH_4NO_3$, and then it is activated by calcination at 1,000° F. in a nitrogen atmosphere.

It is understood that the reaction mixture is not limited to a composition composed of the recited ingredients. Gallium-containing compounds, for example, include gallium sulfate, gallium nitrate, and gallium chloride. The silica source, for example, includes silica hydrosol, silica gel, and silicic acid. The template may be any of the organic templates used to synthesize ZSM-5 catalysts. For example, the template may be tetrapropylammonium hydroxide, tetrapropylammonium bromide or tetrapropylammonium chloride or other organic compounds known to those skilled in the art as successfully-used templates. ZSM-5 catalysts can also be prepared in completely inorganic systems. It is realized that the order of adding or mixing the ingredients is not critical and the reaction mixture can be prepared batchwise or continuously. The critical aspect of this embodiment is that the zeolite reaction mixture contains an $SiO_2/Ga_2O_3$ hydrogel molar ratio of $\geq 100$. The ZSM-5 product obtained from the reaction mixture of the first embodiment is characterized by a framework composed mostly of silicon, oxygen and gallium atoms having an $SiO_2/Ga_2O_3$ ratio of $\geq 100$ and that it contains little or no non-framework gallium. Catalyst containing framework gallium and little or no non-framework gallium can be prepared so that they additionally contain framework aluminum.

In a second embodiment, the ZSM-5 reaction mixture contains the hydrogel molar ratios set forth in Table 1, but $X < 100$. To ensure that the product produced contains gallium, where the gallium is primarily present in the framework of the catalyst and the catalyst contains little or no non-framework gallium, sodium sulfate is added to the zeolite reaction mixture. This reaction mixture may be identical to that of embodiment one except for the starting ratio of $SiO_2/Ga_2O_3$ and for the presence of $Na_2SO_4$. The zeolite reaction mixture is heated to about 100° to 175° C. for six hours to sixty days, preferably from about 150° to 175° C. for twelve hours to eight days, with agitation until a crystalline zeolite is formed. The zeolite produced contains gallium, and the gallium is primarily present in the framework of the catalyst. The catalyst additionally contains silicon and oxygen in its framework and has an $SiO_2/Ga_2O_3$ ratio of less than 100, and contains little or no non-framework gallium. The reaction mixture of this second embodiment is not limited to a composition as recited above, but may be composed of other or additional ingredients as is stated in embodiment one. The reaction mixture of this second embodiment may also contain an aluminum compound so that a resulting ZSM-5 catalyst contains both framework aluminum and gallium and contains little or no non-framework gallium. The critical aspect of this embodiment is that the zeolite reaction mixture must contain an $SiO_2/Ga_2O_3$ molar ratio of $<100$ and an amount of $Na_2SO_4$ so that the $SiO_2/Na_2SO_4$ molar ratio is between $20/1$ to $0.1/1$.

The present inventors have now found that a quantitative amount of sodium sulfate added to a zeolite reaction mixture containing $SiO_2/Ga_2O_3$ molar ratios of less than 100 improves the crystallinity of the product and, thus, the amount of framework gallium in the product. Sodium sulfate is added to the zeolite reaction mixture in the $SiO_2/Na_2SO_4$ molar ratio of between $20/1$ to $0.1/1$ and preferably between $15/1$ to $1/1$. Sodium sulfate is not added to the zeolite reaction mixture of embodiment one, i.e., when the $SiO_2/Ga_2O_3$ ratio of the zeolite reaction mixture is $\geq 100$ because such $SiO_2/Ga_2O_3$ ratios produce products of 100% crystallinity without sodium sulfate.

Generally, the [Ga]ZSM-5 catalysts of this invention have an X-ray diffraction pattern similar to that found in U.S. Pat. No. 3,702,866, and the catalysts of this invention can be manipulated or handled in the same manner as ZSM-5 catalysts containing only framework aluminum as the framework metal. For instance, the [Ga]ZSM-5 catalysts produced by the methods of the first and second embodiments described above can have a wide variety of cations associated therewith, i.e., similar to the cation form found in the aluminum framework-containing zeolites. These cations can be replaced by a wide variety of other cations according to techniques well known in the art. Typical replacing cations include hydrogen, ammonium and metal cations, including mixtures of the same. Of the replacing metallic cations, particular preference is made to cations of such metals as manganese and calcium, as well as metals of Group II of the Periodic Table, e.g., zinc, and Group VIII of the Periodic Table, e.g., nickel.

Typical ion exchange techniques include contacting the ZSM-5 zeolite with a salt of the desired replacing cation or cations. Although a wide variety of salts can be employed, particular preference is given to chlorides, nitrates and sulfates.

Representative ion exchange techniques are disclosed in a wide variety of patents, including U.S. Pat. Nos. 3,140,249, 3,140,251 and 3,140,253.

Following contact with a salt solution of the desired replacing cation, the zeolites are then preferably washed with water and dried at a temperature ranging from 150° to 600° F. and thereafter calcined for activation in air or inert gases at temperatures ranging from about 500° to 1,500° F. for periods of time ranging from one to forty-eight hours or more.

Regardless of the cations replacing the sodium or either alkali metals, in the synthesized form of the [Ga]ZSM-5 catalyst of the invention, the spatial arrangement of gallium, silicon and oxygen atoms, which form the basic crystal lattice, remains essentially unchanged by the described replacement of sodium and/or alkali metal as determined by taking an X-ray powder diffraction pattern of the ion-exchanged material. Such an X-ray diffraction pattern of an ion-exchanged [Ga]ZSM-5 reveals a pattern substantially the same as that set forth in U.S. Pat. No. 3,702,886.

The [Ga]ZSM-5 catalysts prepared by the instant invention are formed in a wide variety of particle sizes. Generally speaking, the particles can be in the form of a powder, a granule, or a molded powder, such as an extrudate having a particle size sufficient to pass through a 2-mesh (Tyler) screen and retained on a 400-mesh (Tyler) screen. In cases where the catalyst is molded, such as by extrusion, the product can be extruded before drying or partially dried and then extruded.

As in the case of many other zeolite catalysts, it may be desirable to incorporate in the [Ga]ZSM-5 other materials resistant to temperatures and conditions employed in organic conversion processes. Such materials include active and inactive materials and synthetic or naturally-occurring zeolites, as well as inorganic materials such as clays, silica, and/or metal oxides. The latter may be either naturally occurring or in the form of gelatinous precipitates including mixtures of silica and metal oxides. The use of an active material in combination with a ZSM-5 catalyst can improve the conversion and/or selectivity of the catalysts in certain organic conversion processes. Inactive materials combined with the catalyst serve as diluents to control the amount of conversion in a given process so that products can be obtained economically and in an orderly manner without employing other means for controlling the rate of reaction. Normally, zeolite materials have been incorporated into naturally-occurring clays, for example, bentonite and kaolin, to improve the crush strength of the catalyst under commercial operating conditions. These materials, i.e., clays, oxides, etc., function as binders for the catalyst. It is desirable to provide a catalyst having good crush strength, because in the environment where these catalyst find use, i.e., in a petroleum refinery, the catalyst is subjected to rough handling which tends to break the catalyst down into powder- like materials causing problems in processing.

Naturally-occurring clays which can be composited with the [Ga]ZSM-5 catalysts of this invention include montmorilloinite and kaolin family members including the sub-bentonites and the kaolins commonly known as Dixie McNamee-Georgia and Florida clays or others in which the main mineral constituent is halloysite, kaolinite, dickite, nacrite, or anauxite. Such clays can be used in their raw state as originally mined or initially subjected to calcination and acid-treated.

In addition to the foregoing materials, the [Ga]ZSM-5 catalysts can be composited with a porous matrix material, such as silica-alumina, silica-magnesia, silica-zirconia, silica-beryllia, silica-titania, as well as ternary compositions such as silica-alumina-zirconia, silica-alumina- thoria, silica-alumina-magnesia, and silica-magnesia-zirconia. The matrix can be in the form of a co-gel.

The catalyst of this invention can be used for the production of high-octane gasoline products. The catalyst shows high activity i.e., selectivity and conversion and improved stability for reactions, such as cracking and light paraffin upgrading, preferably light paraffin upgrading. More particularly, the catalyst can be used for converting $C_2$ to $C_{12}$ paraffins, olefins and naphthenes to high-octane aromatics. [Ga]ZSM-5 zeolites containing gallium which is primarily present in the framework of the catalyst and which contains little or no non-framework gallium are produced by the methods of Examples 1–6. The zeolite reaction mixtures of these examples contain the following hydrogel ratios:

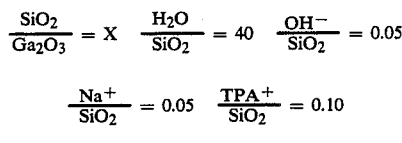

$$\frac{SiO_2}{Ga_2O_3} = X \quad \frac{H_2O}{SiO_2} = 40 \quad \frac{OH^-}{SiO_2} = 0.05$$

$$\frac{Na^+}{SiO_2} = 0.05 \quad \frac{TPA^+}{SiO_2} = 0.10$$

wherein X is varied in ratios of greater than 100 to 1 according to Examples 1–6 set forth below.

EXAMPLE 1

In Example 1, the $SiO_2/Ga_2O_3$ starting ratio used was 100/1. A ZSM-5 catalyst containing framework gallium was prepared by mixing 48.0 grams of silica sol (30.0% silica) with a solution containing 1.03 grams of $Ga_2(SO_4)_3$ and 0.48 grams of NaOH in 139 grams of water. 6.38 grams of tetrapropylammonium bromide was added to the mixture and the pH was checked and adjusted to between pH 12–12.5 by the addition of small amounts of sodium hydroxide. This zeolite reaction mixture was placed in an autoclave and heated at 145°–150° C. and autogenous pressure for two to three days. The product was established as being 100 percent crystalline. Ga- NMR, as explained below, has shown that this product contains gallium which is present primarily in the framework of the catalyst and that the catalyst contains little or no non-framework gallium.

EXAMPLES 2–5

Examples 2, 3, 4 and 5 were conducted in accordance with the procedure of Example 1, except that the $SiO_2/Ga_2O_3$ molar ratio, of X in the zeolite reaction mixture, for Examples 2–5, respectively, was 200/1, 250/1, 350/1, and 500/1. The starting amounts of $Ga_2O_3$ are listed in Table 2.

The crystallinity of all of these products was determined to be 100%. Ga-NMR has shown that these products contain gallium which is present primarily in the framework of the catalysts and that these catalysts contain little or no non-framework gallium.

EXAMPLE 6

Example 6 was conducted in accordance with the procedures of Examples 1–5. However, the method differs from Examples 1–5 by the use of an $SiO_2/Ga_2O_3$ molar ratio of <100 in the presence of an amount of sodium sulfate to give a desired product. In a typical preparation, a mixture containing 27.8 grams of silica gel (30.0% silica) in 40 grams of water and in the presence of 6.0 grams of NaOH was mixed with 2.2 grams of $Ga_2(SO_4)_3$ wherein the $SiO_2/Ga_2O_3$ hydrogel mole ratio equals 90. 46 grams of $H_2O$ and 10.6 grams of $H_2SO_4$ were added to the reaction mixture along with 12.3 grams of tetrapropylammonium bromide and 9.7 grams of sodium sulfate. The pH of the mixture was adjusted to 10 with sodium hydroxide. The mixture was placed in an autoclave and heated at 160° C. and autogenous pressure for seven days.

Ga-NMR has shown that the product obtained by this method contains gallium which is primarily present in the framework of the catalyst and that the catalyst contains little or no non-framework gallium.

EXAMPLE 7

In Example 7, synthesis of a zeolite product in the presence of gallium was conducted in accordance with Example 6 except sodium sulfate was not added to the reaction mixture. In a typical preparation, a mixture containing 27.8 grams of silica gel (30.0% silica) in 86 grams of water was mixed with 2.2 grams of $Ga_2(SO_4)_3$ in 84 grams of $H_2O$ (wherein the $SiO_2/Ga_2O_3$ hydrogel molar ratio equals 90). To this mixture was added 10.6 grams of $H_2SO_4$ and 12.3 grams of tetrapropylammonium bromide. The resulting mixture was adjusted to pH 10 with sodium hydroxide solution to prepare a zeolite reaction mixture. The zeolite reaction mixture was placed in an autoclave and heated at 160° C. and autogenous pressure for seven days.

Ga-NMR has shown that this product contains significant amounts of non-framework gallium, i.e., it contains 47% of the total gallium content of the zeolite product.

Nuclear Magnetic Resonance (NMR) is a proven effective tool for identifying, and quantitatively determining, the presence of gallium in the framework of zeolite materials. The identification of the presence of framework gallium in such materials using NMR is called Ga-NMR. The use of Ga-NMR to determine framework gallium is described in the *Journal of Molecular Catalysis*, 1985, 31, 355, the disclosure of which is incorporated by reference herein. The Ga-NMR spectrum has a single broad line with a chemical shift of 155 ppm and the intensity of the Ga-NMR signal, and the value of the chemical shift correspond to the gallium nuclei in the tetrahedral oxygen environment of the zeolite. The conclusion that a [Ga]ZSM-5 product contains gallium primarily present in the framework of the catalyst and which contains little or no non-framework gallium is based on measuring gallium content by Ga-NMR and comparing this measurement with the overall gallium content for a given sample as determined by elemental analysis.

For instance, if the Ga-NMR determination equals that of the elemental gallium analysis for a given sample, it is concluded that the product contains framework gallium. However, if the Ga-NMR determination exceeds that of the elemental gallium analysis for a given sample, it is concluded that the product contains gallium primarily present in the framework of the catalyst and that the catalyst contains little or no non-framework gallium. If the Ga-NMR determination is less than the gallium elemental analysis, the product contains both framework and a significant amount of non-framework gallium. The amount of non-framework gallium in this third method is determined by subtracting the Ga-NMR determination from the Ga elemental analysis result.

Table II sets forth the results showing that the [Ga]ZSM-5 catalyst synthesized in Examples 1–5 and 6 show that the zeolite produced contains gallium which is primarily present in the framework and that the catalysts contain little or no non-framework gallium. This result is contrasted with the result obtained by the method of Example 7. The catalyst produced by the method of Example 7 contains both framework and significant amounts of non-framework gallium.

TABLE II

Ga-MASNMR and Analytical Data for Determining Presence of Framework Gallium in [Ga]ZSM-5 Samples

| | Starting Grams $Ga_2(SO_4)_3$ | Starting Molar Ratio $SiO_2/Ga_2O_3$ | % Ga, NMR | % Ga, Anal. | % Non-Framework Ga | % $Al_2O_3$, Anal. |
|---|---|---|---|---|---|---|
| Ex. 1 | 1.03 | 100/1 | 2.3 | 2.04 | 0 | 0.058 |
| Ex. 2 | 0.51 | 200/1 | 1.6 | 1.34 | 0 | 0.065 |
| Ex. 3 | 0.41 | 250/1 | 0.88 | 0.79 | 0 | 0.666 |
| Ex. 4 | 0.29 | 350/1 | 0.67 | 0.58 | 0 | 0.064 |
| Ex. 5 | 0.21 | 500/1 | 0.46 | 0.43 | 0 | 0.068 |
| $SiO_2/Ga_2O_3$ ratio | | | 100 with the addition of sodium sulfate. | | | |
| Ex. 6 | 2.2 | 90/1 | 1.6/1.0* Avg. = 1.3 | 1.16 | Avg. = 0 | 0.037 |
| | | | Previous two conditions for $SiO_2/Ga_2O_3$ not met. | | | |
| Ex. 7 | 2.2 | 90/1 | 0.81 | 1.54 | .47 | 0.010 |

*Two NMR determinations.

The [Ga]ZSM-5 catalysts produced in Examples 1 to 5 and 6 having gallium present primarily in the framework and which contains little or no non-framework gallium can be used in the production of high octane gasoline products. The catalysts show high activity and improved stability over catalysts which contains non-framework gallium in reactions such as light paraffins upgrading. More particularly, the catalysts produced by the methods recited above have been found to be catalysts which actively catalyze $C_2$–$C_{12}$ hydrocarbon feedstock to aromatic compounds. Specifically, $C_2$–$C_{12}$ paraffins, olefins and naphthenes can be readily converted to aromatic compounds having high octane ratings such as benzene, toluene, xylenes and mixtures thereof with the catalyst of the claimed invention.

EXAMPLE 8

N-hexane and the [Ga]ZSM-5 catalyst prepared in accordance with Example 6 were charged into a reactor which was adjusted to 538° C. at atmospheric pressure at a liquid hourly space velocity of 0.59. The activity of this catalyst is measured by percent conversion. Percent conversion is defined as $100-C_2=+$ aromatizables and $C_2=+$ aromatizables is defined as all non-aromatic hydrocarbons except methane and ethane. In a first run, the catalytic reaction yielded thirty-five percent by weight of aromatics and twenty-seven percent weight of $C_1$ to $C_2$ paraffins with a sixty-two percent conversion of the feed.

FIG. 1 is a plot showing the weight percent yield of aromatics at various conversion percentages for starting material hexane, identified as an aromatizable, using the catalyst of Example 6. The plotted points of FIG. 1 are in Table III below:

TABLE III

| | CONVERSION DATA | |
|---|---|---|
| | Aromatics Yield Wt % | $100-C_2=+$ |
| 1st Cycle | | |
| 1 | 35 | 62 |
| 2 | 38 | 62 |
| 3 | 33 | 48 |
| 4 | 14 | 28 |
| 2nd Cycle | | |
| 1 | 37 | 61 |
| 2 | 38 | 60 |
| 3 | 33 | 58 |
| 4 | 32 | 56 |

In the first cycle above, the catalyst converts hexane to aromatic products and aromatic intermediates which subsequently produce aromatics. As it seen from the plot, conversion decreases as the catalyst remains on line. The catalyst was regenerated and was used in Cycle 2.

Figure 2:
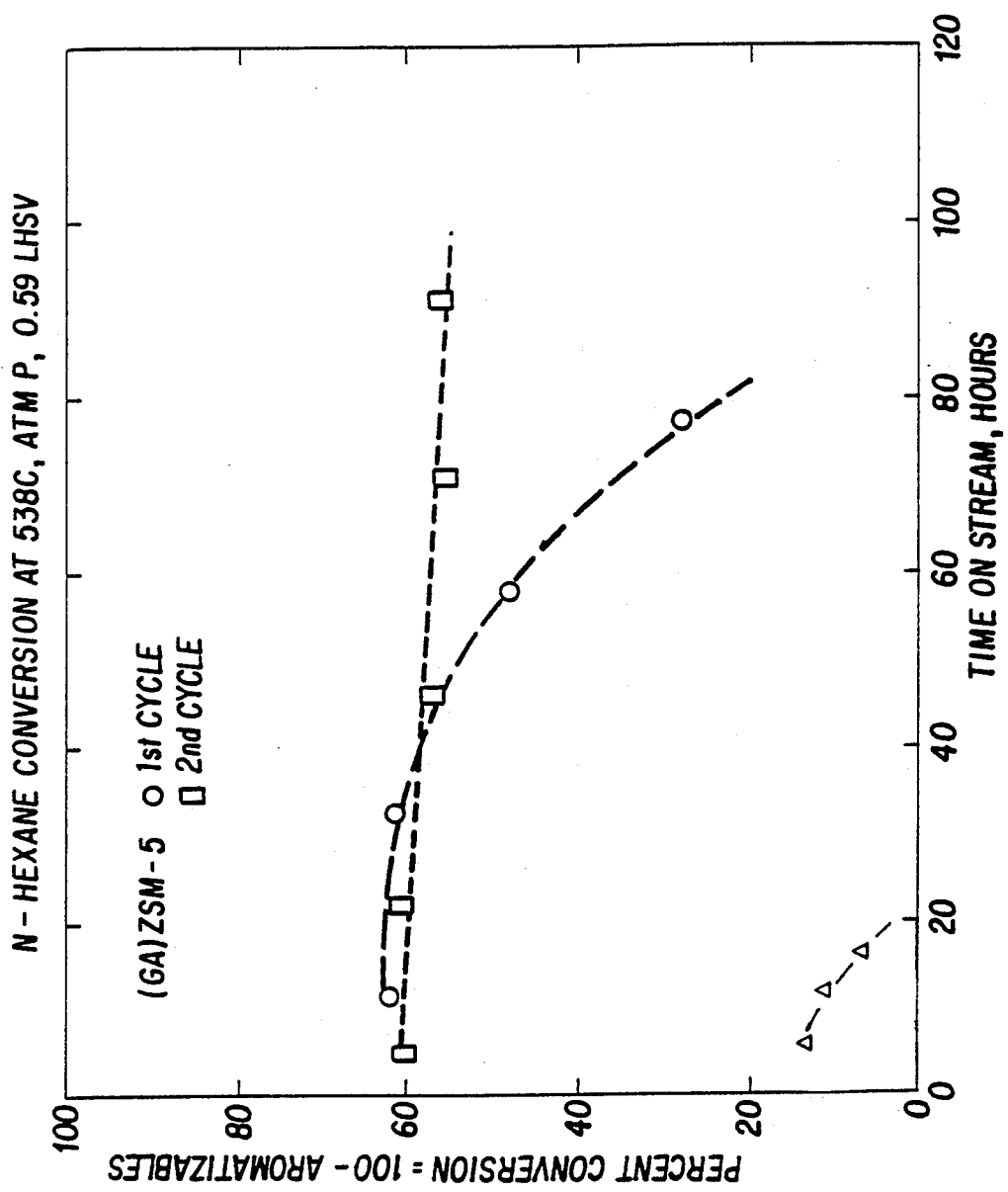
FIG. 2 is a plot showing the aging rate of [Ga]ZSM-5 catalyst produced by the methods of the claimed invention in converting n-hexane to aromatic compounds. A second cycle of the catalyst shows improved aging over a first cycle of the catalyst. Aging data are also plotted for a second catalyst containing only non-framework gallium.

Catalysts produced by the methods of the claimed invention, i.e., catalysts containing gallium where the gallium is primarily present in the framework and which contains little or no non-framework gallium, have been found to have an improved aging rate. FIG. 2 is an aging plot of conversion of n-hexane to aromatic compounds versus time on stream. The plotted points of FIG. 2 are reproduced in Table IV below. The catalyst was used for 90 hours in a first cycle and its activity, i.e., the conversion of n-hexane to products, rapidly decreased after forty hours of use. However, after the regeneration and the use of this catalyst in a hydrogen atmosphere, the catalyst showed sustained and constant activity for over 100 hours in a second cycle as shown in FIG. 2 and in Table IV below. It has also been determined that catalyst containing non-framework gallium age faster than catalyst containing gallium primarily in the framework of the catalyst and little or no non-framework gallium.

FIG. 2 also plots the aging data for a second catalyst which contains gallium as only non-framework gallium. Such a catalyst, as shown by the plotted points represented as triangles, shows a very poor aging rate, and after only 20 hours on line, the catalyst has aged tremendously.

TABLE IV

| | AGING DATA | |
|---|---|---|
| | % Conversion $100-C_2=+$ | Time on Stream Hours |
| 1st Cycle | | |
| 2 | 62 | 12 |
| | 62 | 35 |
| | 48 | 60 |
| | 28 | 78 |
| 2nd Cycle | | |
| | 61 | 22 |
| | 60 | 48 |
| | 58 | 75 |
| | 56 | 95 |

Catalyst regeneration is well-known in the art. Initial regeneration is usually accomplished by contacting the catalyst with elemental $H_2$ at temperatures between 800° F. and 1000° F. (427° C. to 538° C.). Hydrogen regeneration usually removes soft deposits of coke. Hydrogen regeneration, however, does not always completely restore the original level of catalyst activity and oxygen regeneration is used to burn hard coke residue off the catalyst. Catalyst regeneration is described in U.S. Pat. No. 4,276,437, the disclosure of which is herein incorporated by reference.

Examples 9 and 10 are from Ser. No. 258,091, filed Oct. 10, 1988.

The light olefin ($C_2$-$C_5$ olefins) conversions described in Example 10 were conducted in accordance with the invention in the presence of a gallium containing silicate produced as described in Example 9.

EXAMPLE 9

(a) The standard procedure for producing an aluminum containing ZSM-5 composition was followed except the source of aluminum, specifically $Al_2(SO_4)_3$, in that preparation was replaced by $Ga_2(SO_4)_3$ as a course of gallium. The silicon component for zeolite production was provided as 50 grams Q brand silica in 50 grams of water. The gallium source was provided as a solution of 1.11 grams $Ga_2(SO_4)_3$, 84.2 grams water and 5.3 grams of $H_2SO_4$; 6.16 grams of TPA Br (tetrapropylammonium bromide) was used. The $Si/Ga_2$ ratio of the reaction mixture was about 90. The reaction mixture was stirred for several days at 160° C., until product crystallized.

(b) In another procedure for preparing the ZSM-5 containing gallium in its framework, the silica source in the foregoing preparation was replaced by 13.9 grams of extracted $SiO_2$ in 86 grams of water while amounts of other components remained the same as those in the forgoing preparation (a). However, in preparation using extracted silica, stirring of the components for ZSM-5 production was for seven (7) days with addition of 20 cc of 10N NaOH to get a pH of about 10.

(c) In still another preparation, the amount of silica source using extracted silica was doubled. Analysis results of the catalyst compositions of preparations (a), (b) and (c) are set forth below:

TABLE V

| Catalyst | (a) | (b) | (c) |
|---|---|---|---|
| Elemental Analysis (wt %) | | | |
| $SiO_2$ | 97.7 | 96.0 | 95.1 |
| $Al_2O_3$ ppm | 3700 | 86 | 95 |
| Ga | 2.38 | 2.81 | 1.41 |
| Exchange site calc. | | | |
| Meq/g ash | 0.415 | 0.404 | 0.206 |

TABLE V-continued

| Catalyst | (a) | (b) | (c) |
|---|---|---|---|
| TpD meq/g ash | 0.416 | 0.322 | 0.1955 |
| % Ga in framework | 100 | 80 | 95 |
| Alpha | 55 | 60 | 40 |

Each of the products of preparations (a) (b) and (c) of this example exhibited high crystallinity ZSM-5 X-ray diffraction patterns.

(d) In this preparation, the gallosilicate is produced in accordance with our copending application Ser. No. 688,398 filed Jan. 2, 1985. A 6 g of HZSM-5 ($SiO_2/Al_2O_3=26,000/1$) was mixed with 300 cc 0.2N NaOH solution containing 1.5 g of $Ga_2(SO_4)_3$. The mixture was refluxed for 2 hours and then washed, converted into the ammonium form by exchange with $NH_4NO_3$. The resultant zeolite has an exchange capacity of 0.5446 meq/g ash and n-hexane cracking activity of 803.

EXAMPLE 10

In this example, ZSM-5 zeolite containing gallium in the framework, prepared as described above, in accordance with preparation (c) of Example 9, was used in a propylene conversion to produce gasoline distillate and lube range hydrocarbons. A comparative run in which an aluminosilicate ZSM-5 containing no gallium and having an alpha value of 55, was tested in a propylene conversion. The results of these two runs are tabulated in Table VI:

TABLE VI

| | Propylene Conversion T = 230° C. P = 1500 psig | |
|---|---|---|
| Catalyst | [Ga]ZSM-5* | [Al]ZSM-5 |
| Alpha | 40 | 55 |
| WHSV | 0.4 | 0.5 |
| TOS (hrs) | 21 | 22 |
| Products (wt %) | | |
| $C_1$-$C_5$ | 2.3 | 13.0 |
| $C_6$-330° F. | 9.9 | 17.4 |
| 330–650° F. | 58.2 | 58.3 |
| 650° F.+ | 29.6 | 11.3 |

*Prepared by preparation (c) in Example 9 above.

These results indicate that ZSM-5 containing framework gallium produces less light gas and more 650° F.+ hydrocarbons that ZSM-5 free of framework gallium with comparable alpha value.

Table VII below presents comparisons of the 650° F. plus product from runs in which catalyst compositions employing ZSM-5, free of Gallium, of differing alpha values are employed:

TABLE VII

| Catalyst | [Ga]ZSM-5 | | | [Al]ZSM-5 | |
|---|---|---|---|---|---|
| $SiO_2/M_2O_3$ | | 180 | 70/1 | 40/1 | Steamed | 70/1 |
| $M_2O_3$ wt % | | 1.89 | 2.37 | 4.25 | | |
| Alpha | | 40 | 180 | 400 | 55 | |
| Tos (hrs) | 21 | 47 | 19 | 41 | 22 | |
| WHSV | | .04 | | 0.5 | | |
| $C_1$-$C_5$ | 2.3 | 2.2 | 7.0 | 9.7 | 13.0 | |
| $C_6$-330° F. | 9.9 | 9.9 | 16.7 | 10.8 | 17.4 | |
| 330–650° F. | 58.2 | 60.2 | 52.1 | 47.7 | 58.3 | |
| 650° F.+ | 29.6 | 27.7 | 24.2 | 31.6 | 11.3 | |

While specific embodiments of the product, process and method aspects of the invention have been shown and described, it should be apparent that many modifications can be made thereto without departing from the spirit and scope of the invention. Accordingly, the invention is not limited by the foregoing description, but is only limited by the scope of the claims.

What is claimed is:

1. A method of introducing gallium as a zeolitic element in the framework of ZSM-5, wherein the resulting gallium incorporated ZSM-5 is substantially free of non-framework gallium wherein the method comprises
   preparing a ZSM-5 crystallization reaction mixture by
   forming a hydrogel containing a source of $SiO_2$ and a source of $Ga_2O_3$ wherein the $SiO_2$ to the $Ga_2O_3$ is present in a molar ratio of less than 100/1;
   adding to said reaction mixture an amount of $Na_2SO_4$ such that the molar ratio of $SiO_2$ to $Na_2SO_4$ ranges from 20/1 to 0.1/1 and is effective to cause the gallium content of the resulting zeolite to be a zeolitic framework element;
   maintaining said reaction mixture under conditions effective to cause formation of said gallium incorporated ZSM-5 and
   recovering said gallium incorporated ZSM-5.

2. The method of claim 1, wherein the molar ratio of said $SiO_2$ to said $Na_2SO_4$ ranges from 15/1 to 1/1.

3. The method according to claim 1, wherein the zeolite reaction mixture is essentially free of aluminum.

4. The method of claim 2, wherein the zeolite reaction mixture is essentially free of aluminum.

* * * * *